United States Patent [19]

Marder et al.

[11] Patent Number: 4,624,366
[45] Date of Patent: Nov. 25, 1986

[54] CONTAINER

[75] Inventors: Herman L. Marder, Somerville; Ernest E. Lindlar, Old Bridge, both of N.J.

[73] Assignee: Church & Dwight Co., Inc., Piscataway, N.J.

[21] Appl. No.: 300,253

[22] Filed: Sep. 8, 1981

Related U.S. Application Data

[63] Continuation-in-part of Ser. No. 94,194, Nov. 14, 1979, abandoned.

[51] Int. Cl.[4] ............................................. A24F 25/00
[52] U.S. Cl. ................................. 206/620; 239/60; 220/256; 220/257
[58] Field of Search ............ 206/439, 628, 620, 44.12; 220/256, 257; 239/60

[56] References Cited

U.S. PATENT DOCUMENTS

| | | | |
|---|---|---|---|
| 381,824 | 4/1888 | Bowersock | 220/250 |
| 2,039,830 | 5/1936 | Owens | 229/51 |
| 2,180,752 | 11/1939 | Weiss | 239/60 |
| 2,674,018 | 4/1954 | Crippen | 239/60 |
| 3,214,074 | 10/1965 | Schechter | 229/1.5 |
| 3,229,813 | 1/1966 | Crowe, Jr. et al. | 206/439 |
| 3,692,226 | 9/1972 | Young et al. | 229/517 S |
| 4,055,672 | 10/1977 | Hirsch et al. | 206/439 |
| 4,062,486 | 12/1977 | Goodrich | 206/626 |
| 4,124,141 | 11/1978 | Armentrout | 220/306 |

FOREIGN PATENT DOCUMENTS

| | | | |
|---|---|---|---|
| 1103502 | 11/1955 | France | 206/44.12 |

Primary Examiner—Joseph Man-Fu Moy
Attorney, Agent, or Firm—Bierman, Peroff and Muserlian

[57] ABSTRACT

A rigid, three-dimensional container comprising a top portion, a bottom portion and at least one side portion, said side portion having at least one opening covered with gas permeable membrane and means for sealing said opening until the container is ready for use by exposing material in the container to exterior gases such as the atmosphere while keeping the material in the container.

11 Claims, 4 Drawing Figures

CONTAINER

PRIOR APPLICATION

This application is a continuation-in-part of our co-pending, commonly assigned U.S. patent application Ser. No. 94,194 filed Nov. 14, 1979, now abandoned.

STATE OF THE ART

Containers or cartons containing certain powdered material have been used to remove or eliminate objectionable odors. For example, it is a common practice to place boxes of material such as sodium bicarbonate in refrigerators, closets, and the like to absorb undesired odors from food, clothing, etc. One disadvantage of the boxes is that only the top portion of the box opens and only a limited surface area of powdered material is exposed. Another diadvantage is that in the event that such a box is upset, the contents may be distributed in a wholly undesired manner.

Box-like containers or cartons for powder or other pulverized materials are well known. For example, U.S. Pat. No. 1,709,840 relates to powder boxes formed from pasteboard and the like. Containers having non-rectangular shapes are also well known. U.S. Pat. No. Des. 199,206 discloses a five-sided display package having a base broader than the top. Similarly, U.S. Pat. No. Des. 245,479 discloses a display case having a trapezoidal profile.

Cartons or containers having liners are known in the art. U.S. Pat. No. 1,709,840 is directed to a powder box wherein the sides of the box are merely folded together and lining of thin paper prevents the powder from passing between the contacting edges of the walls of the box. According to U.S. Pat. No. 2,200,818, a multiwall container that can be opened for display has a tubular liner. The purpose of the non-permeable liner is to keep the contents fresh or intact when the carbon is opened for display.

OBJECTS OF THE INVENTION

It is an object of the invention to provide an improved three-dimensional container for powdered material having at least one opening to permit air circulation and efficient absorption of contaminants.

It is also an object of this invention to provide a stable container which will retain its contents when tipped comprising a top portion, a bottom portion and at least one side portion, said side portion having at least one opening covered with gas permeable membrane and means for sealing said opening until the container is ready for use by exposing material in the container to exterior gases.

It is further an object of this invention to provide a container which can be manufactured easily and at low cost from a die-cut sheet formable into a threee dimensional configuration, which is readily shippable, and which is easy to use.

These and other objects and advantages of the invention will become obvious from the following detailed description.

THE INVENTION

The three-dimensional container of the invention is comprised of a single blank of material cut and scored to form a top portion, a bottom portion and at least three side portions, with one or more of said side portions having at least one opening covered with a gas permeable membrane capable of holding particles of 10 microns or larger and allowing air passage of 200 to 1000 ft.$^3$/min./ft.$^2$ and means for sealing said opening until the container is ready for use by exposing powdered material in the container to exterior gases while keeping the material in the container.

In one embodiment of the invention, the container is comprised of a three dimensional container with a top portion, a bottom portion and at least 4 side portions, at least one of the side portions having at least one die-cut removable section to form an opening and a gas permeable membrane covering said opening when the die-cut section has been removed. For greater stability, the said container preferably has a trapezoidal shape and preferably, 10 to 90% of the side portions form the openings.

The container of this invention has the advantage over the prior art in that it is a non-spillable container providing a large surface area exposure of powdered material for absorbing contaminants from the atmosphere. The invention provides a low cost container which can be efficiently manufactured, filled, and sealed using existing technology and equipment. Moreover, the container is easily packaged and shipped and is easy to use.

The containers may be comprised of any suitable material, including cardboard, pasteboard, kraft, newsback board, solid bleached sulfate, and the like. It is within the scope of the invention that certain polymeric materials capable of being scored, folded, and die-cut, may be used, such as for example, polyethylene. The useful materials may be wax-coated on one or both sides of the blank.

The container of this invention is useful for containing virtually any gas or moisture absorbing powdered material and typical of such materials are sodium bicarbonate, desiccants and the like. Preferably, the powdered material is an odor-absorbent material such as sodium bicarbonate.

The gas permeable membrane or liner of the invention may be either a complete, or tubular, liner, which may or may not be sealed, or a partial liner covering only the openings. The liner should be affixed or glued to the interior of the carton in such a manner that the perimeter around each opening is sealed.

The membrane must be comprised of any suitable material sufficiently porous or permeable to permit the passage of air at the rate of 200 to 1000, preferably 400 to 800 ft.$^3$/min./ft.$^2$ and may be woven or non-woven fabric or paper and should have sufficiently porosity to keep without sifting powdered contents with a particle size of 10 microns or larger in the container. The membrane also should have a bursting strength in the range of 5 to 30, preferably 10 to 25, pounds per square inch so that it will not rupture in use. Examples of such materials useful as membranes include rice paper, spun woven mats synthetic fibers, non-woven fabrics, etc.

Referring now to the drawings.

Figure 1:
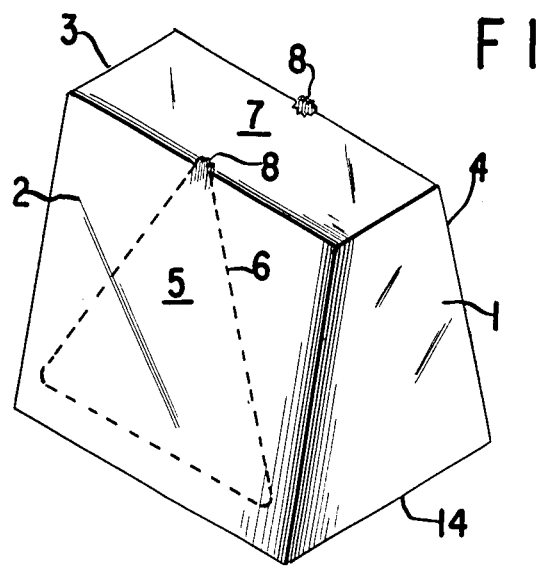
FIG. 1 is a perspective view of one embodiment of the invention wherein die-cut removable sections have not been removed.
Figure 2:
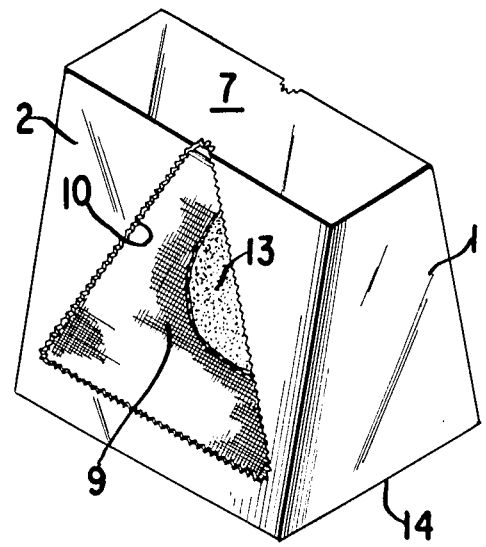
FIG. 2 is a perspective view similar to FIG. 1 wherein the removable sections have been removed.

The embodiment of the invention of FIG. 1 has side walls 1 and 2, shown, as well as side walls 3 and 4, not shown. Side walls 2 and 4 each are provided with a removable section such as section 5 formed by die-cut, perforated line 6. Perforated line 6 encroaches slightly on top section 7 so that a small portion of section 5 protrudes after the carton is formed. A corresponding portion of section 8 on side wall encroaches on top 7 also. FIG. 2 is another view of the embodiment of FIG. 1 after sections 5 and 8 have been removed, and the liner 9 can be seen through opening 10.

Figure 3:
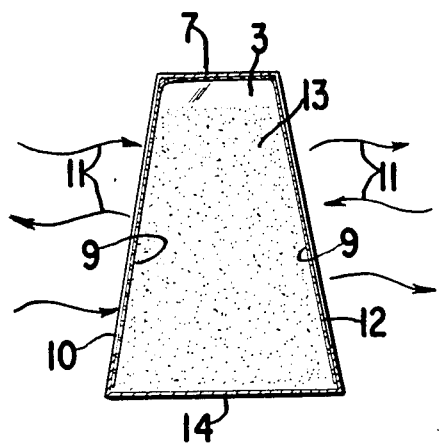
FIG. 3 is a lateral, cross-sectional view showing air circulation.

In the lateral, cross-sectional view of FIG. 3, it can be seen that when the sections 5 and 8 are removed, air circulates as indicated by arrows 11 through openings 10 and 12 into the box and the powdered material 13 therein. Membrane 9 spans openings 10 and 12 and prevents the powdered material 13 from spilling out of the box. Preferably the powdered material 13 is present in an amount sufficient to cover the openings 10 and 12. Also seen in FIG. 3 is bottom section 14, which preferably is larger than top section 7.

Figure 4:
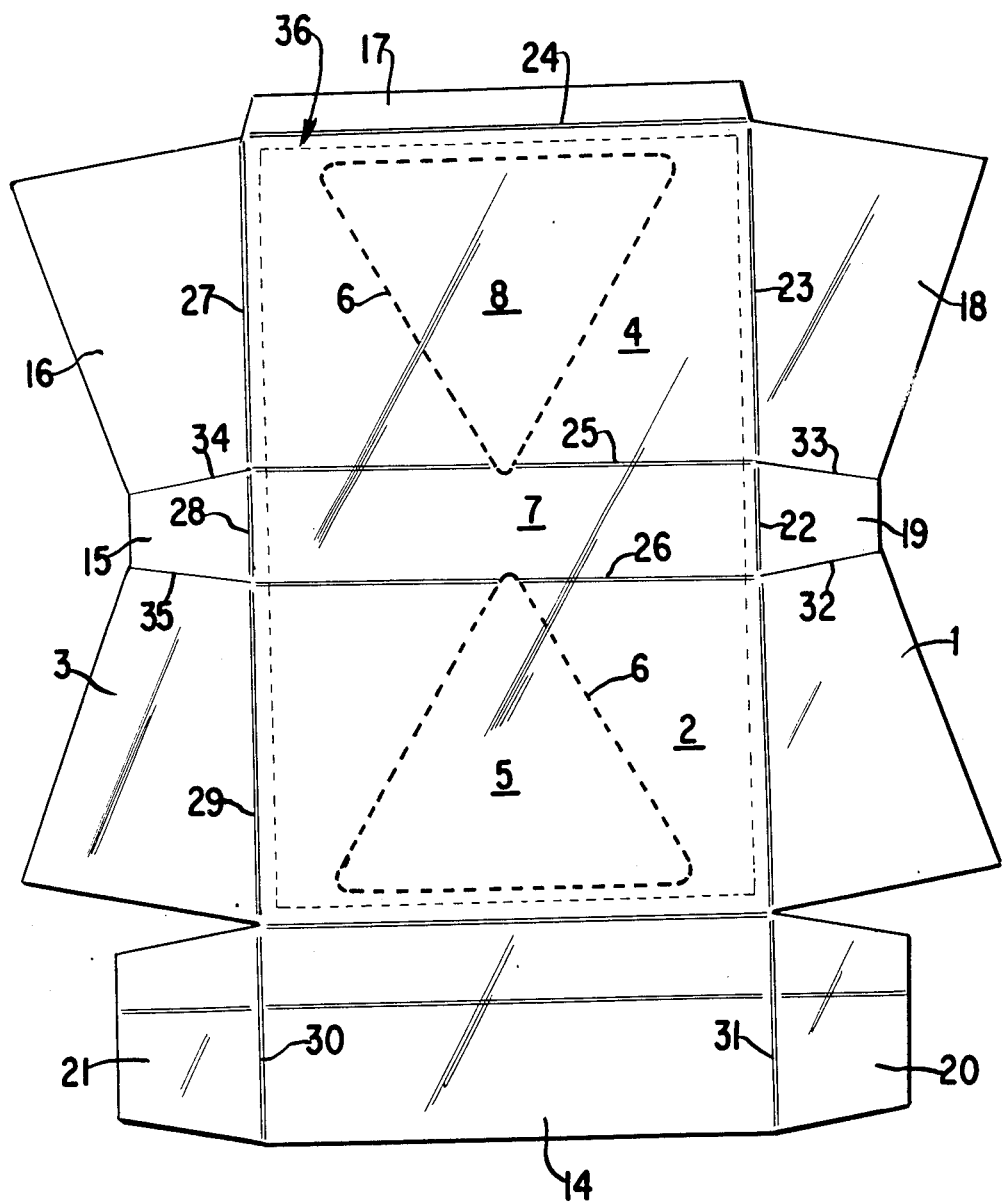
FIG. 4 shows a blank representing an embodiment of the invention as the blank is cut and creased preparatory to folding.

FIG. 4 presents a blank from which the non-spillable carton of FIGS. 1 to 3 can be prepared. Side walls 1,2,3 and 4, top section 7, bottom section 14, and flaps 15 to 21 are formed by score lines 22 to 31 and die-cut lines 32 to 35. In addition, bottom section 14 and flaps 20 and 21 may have a working score line which facilitates assemblage and/or storage of a partially assembled carton. Dotted line 36 indicates areas where line 9 (not shown) may be affixed to the blank prior to folding.

Preferably, the non-spillable container is formed by affixing or gluing flap 17 to flap 14. Then, for example, flaps 15 and 21 may be folded, flap 16 may be folded, and side walls 3 may be folded and affixed or glued to flap 16. The opposite side of the container could be formed in a similar manner after the container is filled with powdered material. The order in which the various surfaces are prepared is not critical, and the container could also be prepared by forming the side walls prior to forming the bottom section.

The non-spillable container of this invention can be almost any shape, including cylindrical, triangular, square, rectangular, pentagonal, octagonal, etc. Preferably the carton will be in a shape that will provide maximum stability, such as when the bottom section 14 is greater than top section 7, and maximum circulation within the powdered material, such as when side walls 2 and 4 are greater than side walls 1 and 3.

The container preferably should contain at least one removable section, preferably at least two removable sections although it is not necessary if there is an overwrap. While the removable sections shown in FIGS. 1 and 4 are triangular, the sections may in fact have almost any shape. Preferably the removable sections will have a portion that will encroach on top section 7 and then protude slightly when the blank is folded. This not only aids in removing the removed sections but also helps prevent damage to the liner.

The sealing means is necessary to preserve the contents of the container until the consumer is ready to use the contents thereof and other sealing means besides the die-cut removable sections may be used. For example, the container may be formed with holes already cut in the side thereof and the entire container may be wrapped in an appropriate material such as cellophane, plastic wrap and the like which will prevent the atmosphere from contacting the contents of the container until it is removed.

It is within the scope of this invention that each outer surface of the carton may have one or more removable sections so long as the liner prevents powdered material from spilling. Various other modifications of the cartons of the invention may be made without departing from the spirit or scope thereof and it is to be understood that the invention is to be limited only as defined in the appended claims.

We claim:

1. A carton containing powdered material capable of absorbing odors in a confined area comprising a top portion, a bottom portion and at least four side portions, with at least two of the opposing side portions having at least one opening therein covered with a sufficiently porous liner to allow free passage of air therethrough while keeping the powdered material in the container and means for sealing said openings until the container is ready for use by exposing material in the container to the atmosphere, the said liner being capable of holding particles with a particle size of 10 microns or larger and having a porosity capable of allowing air passage at a rate of 200 to 1000 ft.$^3$/min./ft.$^2$.

2. A container of claim 1 wherein the sealing means is a die-cut removable section of the side portion to form an opening therein when removed.

3. A container of claim 1 wherein the sealing means is a plastic film surrounding the container.

4. The container of claim 1 wherein the air passage rate is 400 to 800 ft.$^3$/min./ft.$^2$.

5. The container of claim 1 wherein the bursting strength of the liner is 5 to 30 pounds per square inch.

6. The container of claim 1 wherein the bursting strength of the liner is 10 to 25 pounds per square inch.

7. A method of removing odors from a confined space comprising removing from a carton of claim 1 the means for sealing the openings and placing the carton in the confined space whereby the powdered material is exposed to the atmosphere in the confined space and odors are absorbed.

8. The method of claim 7 wherein the confined space is the interior of a refrigerator.

9. A container of claim 2 wherein the die-cut removable section extends into the top portion to form a tab for easy removal of the die-cut section.

10. A container of claim 1 wherein the liner is a partial liner covering the openings on the side of the container.

11. A container of claim 1 wherein the bottom portion is larger than the top portion.

* * * * *